United States Patent [19]
Krueger et al.

[11] Patent Number: 5,776,187
[45] Date of Patent: Jul. 7, 1998

[54] COMBINED HOLDER TOOL AND ROTATOR FOR A PROSTHETIC HEART VALVE

[75] Inventors: Kurt D. Krueger, Stacy; Averdon M. DeLeon, Shoreview, both of Minn.; William S. Nettekoven, Sandy, Utah; Kimberly A. Anderson, Eagan; Michael J. Girard, Lino Lakes, both of Minn.

[73] Assignee: St. Jude Medical, Inc., St. Paul, Minn.

[21] Appl. No.: 692,396

[22] Filed: Aug. 5, 1996

Related U.S. Application Data

[63] Continuation-in-part of Ser. No. 385,785, Feb. 9, 1995, abandoned.

[51] Int. Cl.⁶ .................................................. A61F 2/24
[52] U.S. Cl. ............................................................ 623/2
[58] Field of Search ........................................ 623/2, 900

[56] References Cited

U.S. PATENT DOCUMENTS

| | | |
|---|---|---|
| 3,828,787 | 8/1974 | Anderson et al. ............... 623/2 X |
| 4,679,556 | 7/1987 | Lubock et al. ................... 606/1 |
| 4,683,883 | 8/1987 | Martin ......................... 623/2 X |
| 4,755,181 | 7/1988 | Igoe ............................ 623/2 |
| 4,865,600 | 9/1989 | Carpentier et al. ............. 623/2 |
| 5,236,450 | 8/1993 | Scott ........................... 623/2 |
| 5,403,305 | 4/1995 | Sauter et al. .................. 606/1 |
| 5,480,425 | 1/1996 | Ogilive ......................... 623/2 |

*Primary Examiner*—David H. Willse
*Attorney, Agent, or Firm*—Hallie A. Finucane, Esq.

[57] ABSTRACT

The invention relates to a holder/rotator device which may be used to hold and then rotate a heart valve prosthesis during implantation of the heart valve prosthesis. The device comprises holder/rotator which includes a post and a rotator head, and a handle. The rotator head comprises a gripping surface of a material which engages and grips the surface of the heart valve prosthesis and facilitates the smooth rotation of the valve.

19 Claims, 8 Drawing Sheets

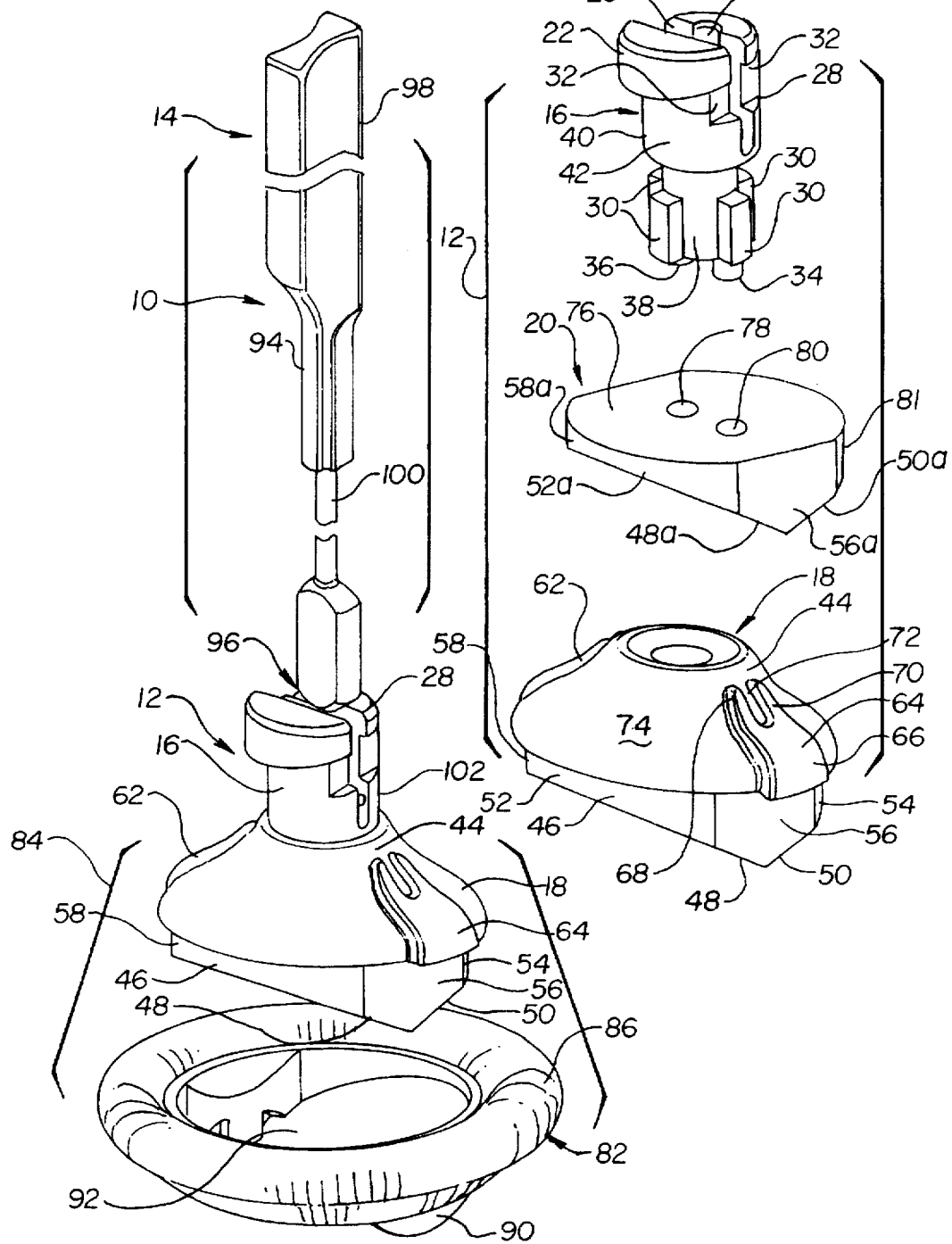

COMBINED HOLDER TOOL AND ROTATOR FOR A PROSTHETIC HEART VALVE

This is a Continuation-In-Part application of U.S. Ser. No. 08/385,785, filed on Feb. 9, 1995, now abandoned.

FIELD OF THE INVENTION

The invention relates to a combined device which may be used as a holder for a heart valve prosthesis and also as a rotator mechanism to position the prosthesis within the patient. In particular, the invention relates to a device having a gripping surface comprising a material which may be used to engage and grip the surface of a rotatable mechanical heart valve, facilitating the smooth rotation of the valve.

BACKGROUND OF THE INVENTION

Rotator tools to rotate a prosthesis in-situ are known. These rotator tools include a rotator head which engages the prosthesis, such as a mechanical heart valve. The rotator head generally comprises a rigid material, such as a plastic, which may cause damage to the leaflets of the heart valve and which may slip when there is blood on the valve and friction is insufficient. In general, the accessories currently available function either as a valve holder for the heart valve, or as a rotator tool to rotate the prosthesis within the patient, and are disposable.

A valve rotator currently available from CarboMedics, Inc., is used solely to rotate the prosthetic heart valve in-situ and does not function as a combined valve holder and rotation tool. The device comprises a hard plastic material.

A device is available from Medtronic, Inc. that may be used as both a rotator tool and a valve holder. This device is used only with a single disc occluder valve having a rotatable sewing ring. The device onto which the heart valve is sutured, comprises a rigid plastic material. Aortic valves, however, require manipulation of the occluder prior to use of this device.

A hard plastic holder/rotator device available from Duromedics, Inc. uses two retaining sutures to secure the holder/rotator to the heart valve sewing ring through a collar ring. The retaining suture provides traction counter to the rotation desired. Handles threaded into the holder/rotator are used for counter-clockwise rotation of the valve relative to the sewing ring. The valve may alternately be rotated by hand relative to the sewing ring.

SUMMARY OF THE INVENTION

The invention relates to a device for engaging and gripping a heart valve prosthesis having an annulus and at least one leaflet. The device includes an upstanding post made of a rigid material. In addition, the device includes a head coupled to the post which includes a gripping surface made of a soft material. The gripping surface of the head may be angled or arched. The gripping surface is adapted to be substantially adjacent the annulus of the heart valve prosthesis and is in parallel relation with the leaflet so that the head can grip and engage the heart valve prosthesis to facilitate positioning of the heart valve prosthesis during implantation.

The invention also relates to the combination of a heart valve prosthesis and a device for gripping and engaging the heart valve prosthesis during implantation. The heart valve prosthesis has an annulus with an annular aperture and at least one leaflet. The device has a post comprised of a rigid material and a head having a gripping surface comprising a soft material. The gripping surface is adapted to be substantially adjacent the annulus of the heart valve prosthesis and is in parallel relation with the leaflet so that the head can grip and engage the heart valve prosthesis to facilitate positioning of the heart valve prosthesis during implantation.

BRIEF DESCRIPTION OF THE DRAWINGS

FIG. 1 is a perspective view of a valve holder/rotator tool constructed in accordance with teachings of the invention positioned above an aortic mechanical heart valve.

FIG. 2 is an exploded fragmentary view of the components comprising the mechanical heart valve holder/rotator tool shown in FIG. 1.

DETAILED DESCRIPTION OF THE PREFERRED EMBODIMENTS

Figure 3:
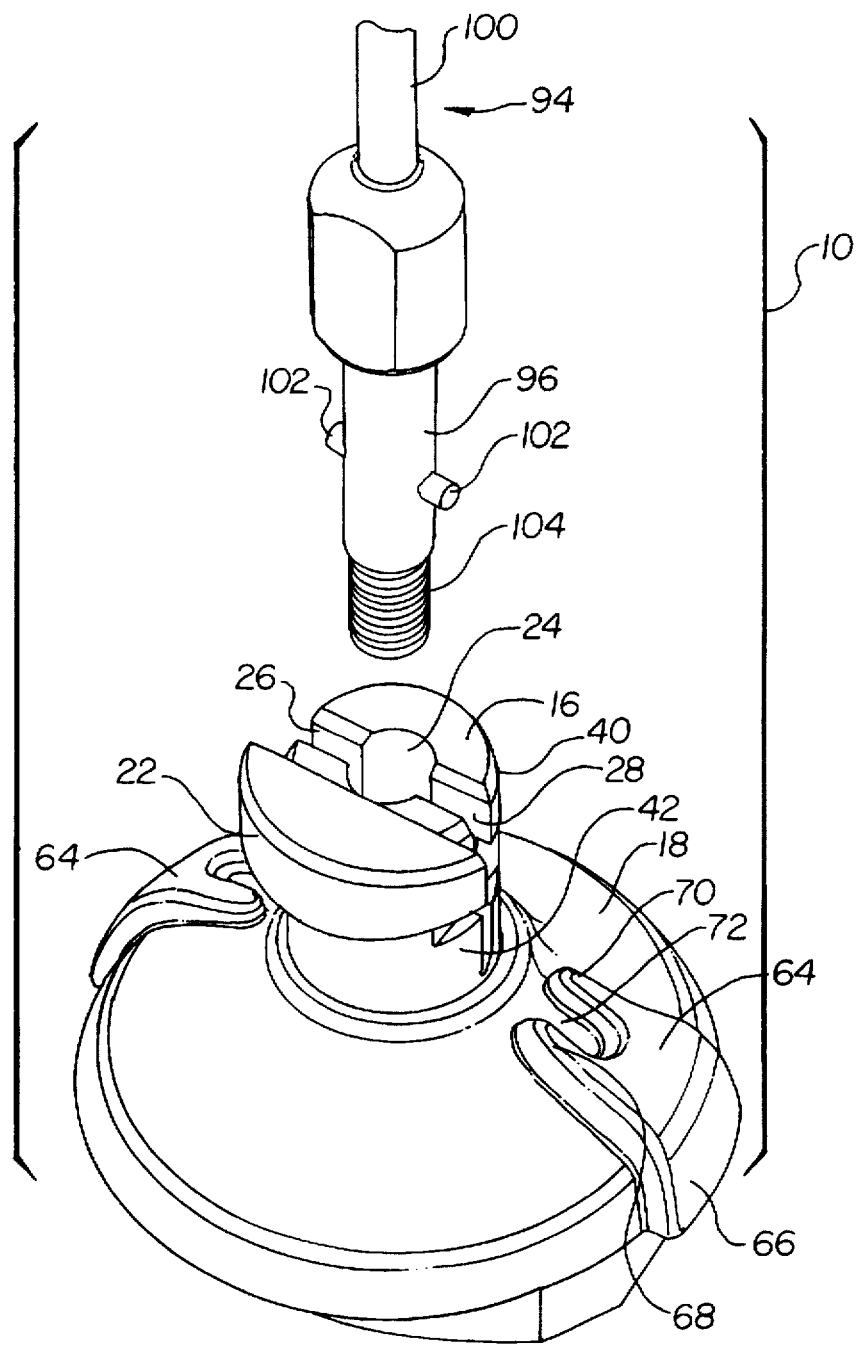
FIG. 3 is a perspective view of the holder/rotator tool of the present invention used with the handle.

The invention relates to a device which is a combined heart valve holder and rotator tool which may be used to position and rotate a heart valve prosthesis during implantation of the heart valve prosthesis. For the purposes of this description of the invention, the holder/rotator tool will be described generally with regard to its use with a rotatable, bi-leaflet mechanical heart valve which has an annulus with a substantially annular aperture. Referring to FIG. 1, the holder/rotator tool assembly 10 generally comprises holder/rotator 12 and holder handle 14. The mechanical heart valve, such as a rotatable aortic valve 82 shown in FIG. 1, is positioned on and secured to the valve holder/rotator tool assembly 10 by sutures (not shown in FIG. 1). After the heart valve is positioned in the patient using the valve holder/rotator tool 10, the sutures joining the heart valve to the tool 10 are cut, and the tool 10 is removed.

The holder handle 14 comprises handle portion 94, which the surgeon holds during implantation, and handle rod or tip 96, which engages the holder/rotator 12 as shown in FIG. 1. The handle tip 96 itself is shown in detail in FIG. 3. The handle portion 94 includes a grip 98 and an elongated central section 100. To facilitate gripping, the grip 98 is generally rectangular in cross section, although other handle grip configurations are contemplated by this invention. The grip 98 may be fabricated from a biocompatible, durable material, such as Radel®.

In order to permit the surgeon to easily and accurately position the valve in the patient, the central section 100 is malleable. In this way, the malleable section 100 may be bent to a desired position to aid in implantation. According to one aspect of the invention, the holder handle 14 may be reused after sterilization. Thus, the malleable section 100 of handle 94 may be fabricated from an appropriate shape memory alloy material, such as Tinel® (Raychem Corporation in California). In this way, because the malleable section is made of a shape memory alloy, the malleable section 100, which may have been bent to an appropriate position during implantation surgery, will straighten to its original configuration during sterilization prior to subsequent implantation surgery.

In order to engage the holder/rotator 12, the handle tip 96 is provided with a cross pin 102 which extends radially from handle tip 96, which is shown in more detail in FIG. 3. The significance of the cross pin 102 will be explained below in more detail with regard to the holder/rotator 12. In order to facilitate use of the holder. handle 14 with standard, non-rotatable valves, the handle tip 96 is also provided with screw threads 104 at its lowermost end. It will be appreciated by those skilled in the art that the threads 104 may be used to engage standard, non-rotatable valves and remove them from a packaging container without the surgeon or medical personnel touching the valve. The handle tip 96 is formed of a biocompatible, durable, rigid metallic material, such as stainless steel.

Turning now to FIG. 2, an exploded perspective view of the holder/rotator 12 components is shown. The holder/rotator 12 generally comprises an upstanding rotator post 16 and rotator head 18. In order to facilitate suturing of the holder/rotator 12 to the valve, the rotator head 18 comprises a conformable, soft material, such as silicone or an elastomeric material, which encapsulates a portion of the rotator post 16. While not essential to the invention, the holder/rotator 12 may include a stiffening core 20 about which the conformable, soft material is molded to provide additional stiffness to the molded holder/rotator 12 and minimize deformation during rotation.

Describing each of these components in more detail, the rotator post is formed from a rigid and durable material, such as a plastic material. While polyphenylsulfone plastics, such as Radel® R-5100 (Amoco Performance Products in Georgia) has been found acceptable, any biocompatible material with appropriate rigidity or stiffness may be used.

In order to receive the handle tip 96 and cross pin 102 of the holder handle 14, the rotator post 16 is provided with an annular bore or passageway 24, which extends axially through the approximate center of the rotator post 16 and cross pin passageways 26, 28. The cross pin passageways 26, 28 comprise two generally planar passageways positioned on either side of the annular passageway 24, and extend through the side wall 42 of the upper portion 40 of the rotator post 16, and radially from annular passageway 24. As may be seen in FIG. 4, the cross pin passageways 26, 28 taper inward slightly as shown at 26a and then may be slightly wider at its lowermost end 26b. In this way, as the handle tip 96 and cross pin 102 are moved downward into the annular passageway 24 and the cross pin passageways 26, 28, the cross pin 102 may snap securely into place in the lowermost end 26b of the cross pin passageways 26, 28.

The rotator post 16 is additionally provided with a flange 22, which is generally semi-circular in shape and extends outwardly from upper portion 40 of rotator post 16, and grooves 32, which are adjacent the openings of cross pin passageways 26, 28 along upper portion 40 of rotator post 16. The grooves 32 and the flange 22 are generally used to achieve proper packaging orientation and secure the holder/rotator 12 with the valve in the shipping package. It will be appreciated, however, that the flange 22 additionally provides a visual indication of the position of the valve during implantation surgery. Moreover, while it is preferable that the holder handle 14 be used to rotate the holder/rotator 12, the grooves 32 and the flange 22 provide grippable surfaces for the surgeon to directly grasp and rotate the heart valve during the surgery.

In order to provide the desired engagement of the rotator post 16 with the molded rotator head 18, the rotator post 16 is provided with a plurality of integral splines or shoulders 30, which extend outwardly from the lower portion 38 of the rotator post 16, as shown most clearly in FIG. 1. While four splines 30 are provided in the design shown, an alternate number of splines 30 may be provided.

Figure 4:
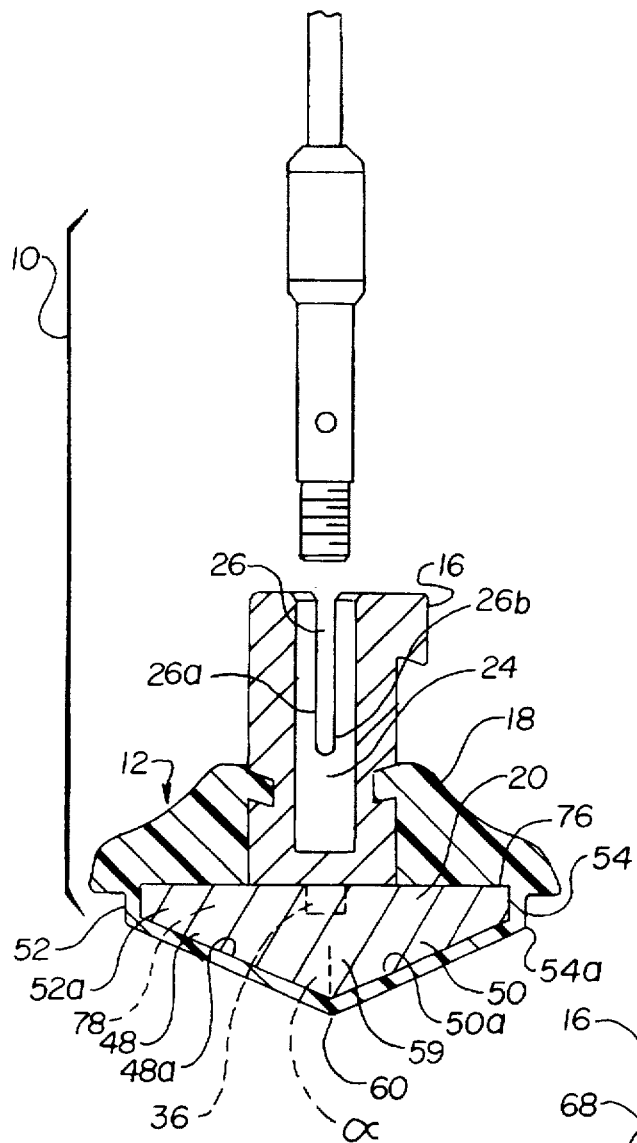
FIG. 4 is a cross-sectional view of the holder/rotator tool shown in FIG. 3 with the handle positioned above the holder/rotator tool.
Figure 5:
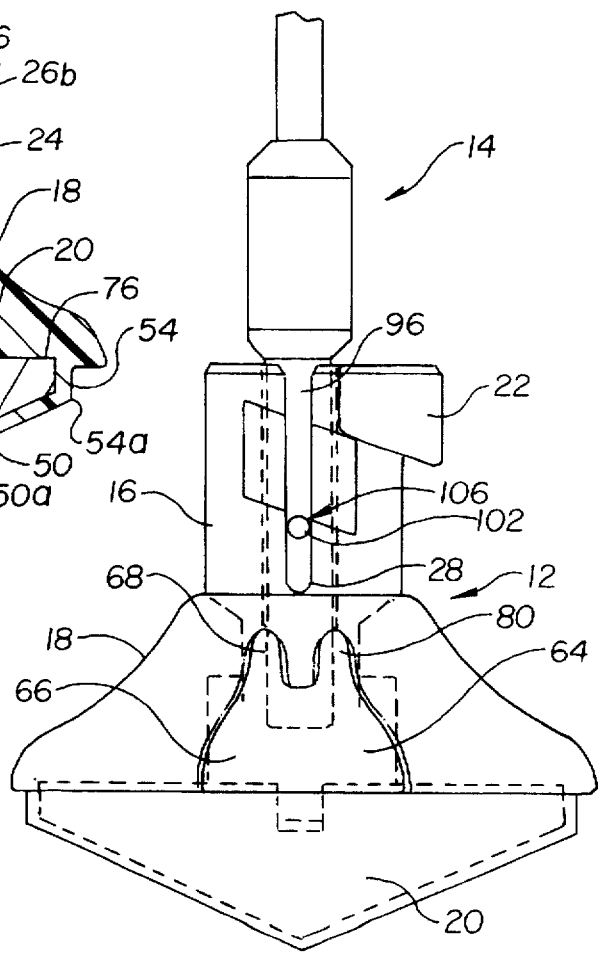
FIG. 5 is a side elevation view of the handle inserted in the holder/rotator tool of the present invention.

As shown in FIGS. 2 and 4, during fabrication, the upper portion 44 of the rotator head 18 is generally molded about the lower portion 38 and the splines 30 of the rotator post 16. It will thus be appreciated that the interaction between the splines 30 and the conformable material of the rotator head 18 generally holds the rotator head 18 and the rotator post 16 in engagement.

In order to ensure an accurate fit between the rotator head 18 and the valve, the shape of the lower portion 46 of the rotator head 18 is determined according to the type of valve with which the holder/rotator 12 is used. The embodiment of the invention shown in FIGS. 1–7 is utilized with an aortic heart valve, and, as a result, the lower portion 46 has angled distal surfaces 48, 50 which taper inwardly. In this way, the lower portion 46 of the rotator head 18 has a gripping surface which substantially conforms to the shape of the heart valve orifice. In other words, the angled surfaces 48, 50 are configured to be in parallel relation with the two leaflets in the mechanical heart valve. The leaflets in the aortic heart valve are in a closed position, such that the leaflets meet at an angle along a diametral line of the annulus or orifice. As best shown in FIG. 4, angled surfaces 48, 50 extend at an angle from annular side walls 52, 54, forming a V-shaped member. The annular side walls 52, 54 extend between vertical side walls 56, 58, as shown in FIGS. 1 and 2. Thus, the angled surfaces 48, 50 are substantially perpendicular to the vertical side walls 56, 58.

In the embodiment shown, the angled surfaces 48, 50 extend at an angle α of about 61 degrees to 66 degrees from a plane 59 at center 66, as shown in FIG. 4. It will be appreciated that the preferred angle of the angled surfaces 48, 50 is dependant upon the particular aortic mechanical heart valve leaflet configuration with which the holder/rotator tool assembly 10 is engaged.

The upper portion 44 of rotator head 18 may be of varying shapes. A bell-shaped or frusto-conical configuration has been found to be an advantageous shape inasmuch as this shape allows enhanced visibility of the valve in-situ for the surgeon or other professional.

Figure 7:
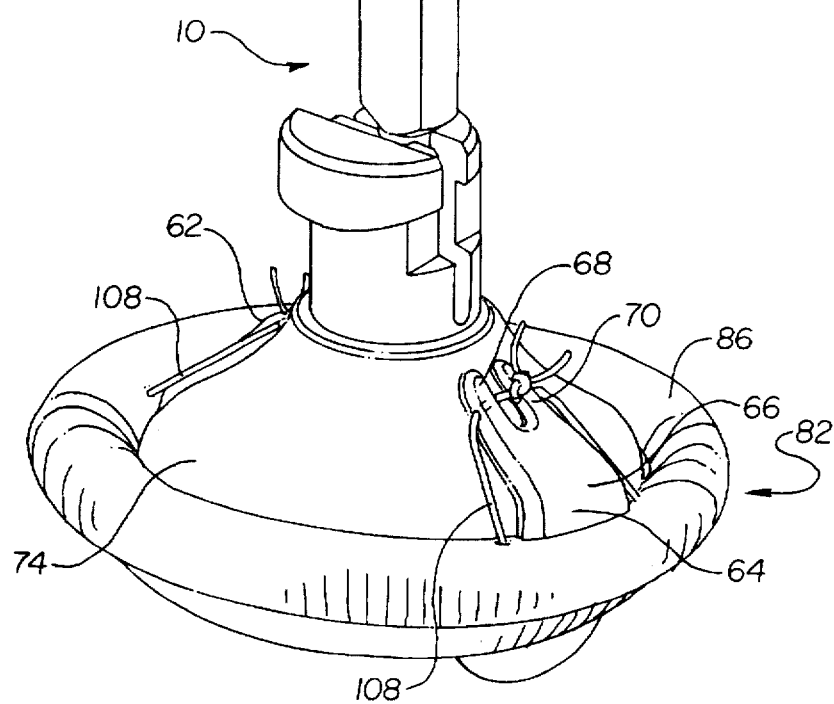
FIG. 7 is a perspective view of the holder/rotator tool and mechanical heart valve assembly with sutures extending between the mechanical heart valve and the rotator head.

According to an important feature of the invention, the upper portion 44 of the rotator head 18 provides suture attachment sites at which the valve may be coupled to the rotator head 18. In the illustrated embodiment, suture shoulders 62, 64 are provided which are integral with upper portion 44, and preferably formed of the same silicone or elastomeric material as the rotator head 18. As shown in FIGS. 1–3 and 7, the suture shoulders 62, 64 are positioned adjacent vertical side walls 56, 58 and are elevated in relation to the surface 74 of upper portion 44 of rotator head 18. The suture shoulders 62, 64 include a base portion 66 and extending fingers 68, 70 separated by a groove 72. It will be appreciated, however, that the specific form of the suture shoulders 62, 64 may vary from the design shown. As shown in FIG. 7, the valve 82 is secured to the rotator head 18 during shipping and surgery by means of sutures 108 which extend through the cuff 86 and fingers 68, 70 of the suture shoulders 62, 64.

The rotator head 18 is generally formed of a conformable and soft, durable biocompatible elastomeric material, such as silicone or a soft plastic, which will not damage, scratch or mar the surface of the valve leaflets. A particularly advantageous material is silicone having a shore A durometer range between 55 and 65, such as SILASTIC® 7-6860 A/B medical grade liquid silicone rubber (Dow Corning).

Figure 6:
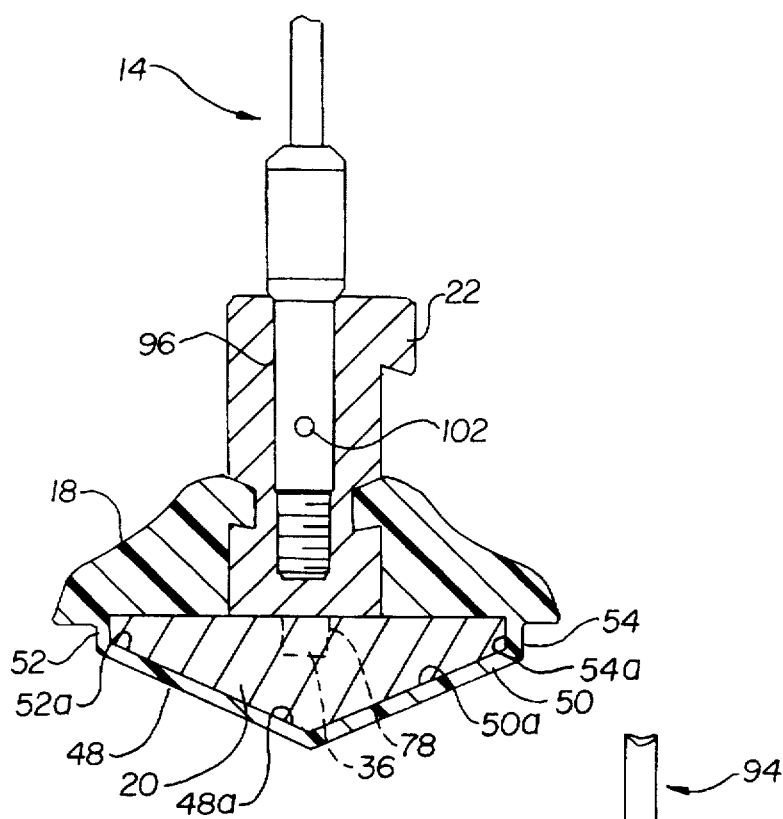
FIG. 6 is a cross-sectional view of the holder/rotator tool in which the handle is inserted.

In order to provide additional stiffness and minimize deformation of the rotator head 18 when rotating a valve, the rotator head 18 may also include and be molded about a stiffening member or core 20, such as shown in FIGS. 2, 4, and 6. The stiffening core 20 is generally configured to the shape of and has the same geometric proportions as the lower portion 46 of the rotator head 18, only smaller. In the illustrated embodiment, the stiffening core 20 comprises a generally planar upper surface 76, vertical side walls 56a, 58a, annular side walls 52a, 54a extending between vertical side walls 56a, 58a, and angled surfaces 48a, 50a.

To secure the stiffening core 20 to the rotator post 16, the stiffening core 20 may be provided with apertures or bores 78, 80, and the rotator post 16 provided with mating studs 34, 36, which extend from and are integral with lower portion 38 of the rotator post 16. As may be seen in FIGS. 4 and 6, the apertures or bores 78, 80 extend into upper portion 81 of stiffening core 20, but do not extend completely through stiffening core 20. While two mating studs 34, 36 and two bores 78, 80 are provided in the drawings, an alternate number of mating studs 34, 36 and bores 78, 80 may be provided.

The stiffening core 20 imparts a greater stiffness to the holder/rotator 12 and increases the amount of torque which may be applied by the holder/rotator tool assembly 10 while maintaining the valve interfacing advantages. The stiffening core 20 is particularly useful with smaller size heart valves.

The stiffening core 20 comprises a generally rigid and durable material, such as a plastic material. Polysulfones such as Udel® or polyphenylsulfones such as Radel® (Amoco Performance Plastics Products) have been found to be acceptable materials.

The operation and use of holder handle 14 and the aortic heart valve holder/rotator 12 shown in FIGS. 1–7 may be summarized by explaining, first, the assembly, molding, and packaging of the holder rotator 12, and second, the utilization of the holder handle 14 by the surgeon or other medical personnel during surgery.

In assembly, if a stiffening core 20 is to be utilized, the studs of the rotator post 16 are positioned within the apertures 78, 80 of the stiffening core 20. The lower portion 38 of the rotator post 16, and the stiffening core 20 (if utilized), is then positioned within a mold. Silicone or another elastomeric material is injected into the mold and cured to form the rotator head 18. The holder/rotator 12 is then removed from the mold.

To form an assembly 84 of the heart valve 82 and the holder/rotator 12, the heart valve 82 is positioned with its closed leaflets 92, 93 (93 not shown) substantially adjacent the angled surfaces 48, 50 of the rotator head 18. There will preferably be a small gap on the order of 0.020 inches (0.5 mm) between the angled surfaces 48, 50 and the leaflets 92, 93. In this position, the vertical side walls 56, 58 align with the pivot guards 88, 90 (88 not shown) of the mechanical heart valve 82, and are in approximate alignment with the suture shoulders 62, 64. Sutures 108 are then positioned between the cuff 86 of the heart valve 82 and the suture shoulders 62, 64 to form a valve holder/rotator tool assembly 84. As may be seen in FIG. 7, the sutures 108 are preferably tied And knotted to at least one of fingers 68, 70 of the suture shoulders 62, 64. In this way, the rotator head 18 is releasably engaged with the heart valve 82. The assembly 84, which includes the holder/rotator 12 and the valve 82, is placed into a packaging container (not shown) having a peel-down lid opening, and is sterilized.

At the time the valve 82 is to be implanted within the patient, the lid of the packaging container is peeled down to expose the assembly 84. As seen most clearly in FIGS. 3–6, the surgeon inserts the handle tip 96 of the holder handle 14 into annular passageway 24 aligning the cross pin 102 with the cross pin passageways 26, 28. The tip 96 is moved downward through the passageways 24, 26, 28 until the cross pin 102 snaps into position in the lower most end 26b of the cross pin passageways 26, 28. After cross pin 102 snaps into position, holder/rotator tool assembly 10 and valve 82 may be removed from the container, without physical contact with the surgeon's hands.

The holder/rotator tool assembly 10 may then be used as a valve holder to place valve 82 within the patient. Handle holder 14 may be bent into a desired orientation to facilitate positioning and placement of valve 82 within the patient. When the correct position of the valve 82 is achieved, the surgeon decouples or cuts sutures 108, which have retained heart valve 82 against rotator head 18. In this way, when the valve is disengaged, the cut sutures 108 remain attached to the rotator head 18 as it is removed. If repositioning of the valve is desired, the holder/rotator tool assembly 10 may then be used to rotate the valve 82 into the correct orientation within the tissue by rotating the annulus of the valve relative to the sewing cuff during implantation.

Upon completion of the procedure, the holder/rotator tool assembly 10, along with the attached sutures 108 is then removed from the heart valve 82. The rotator head 18 and the rotator post 16 are disposed of by the surgeon or other medical personnel, while the holder handle 14 may be sterilized and re-used.

Figure 8:
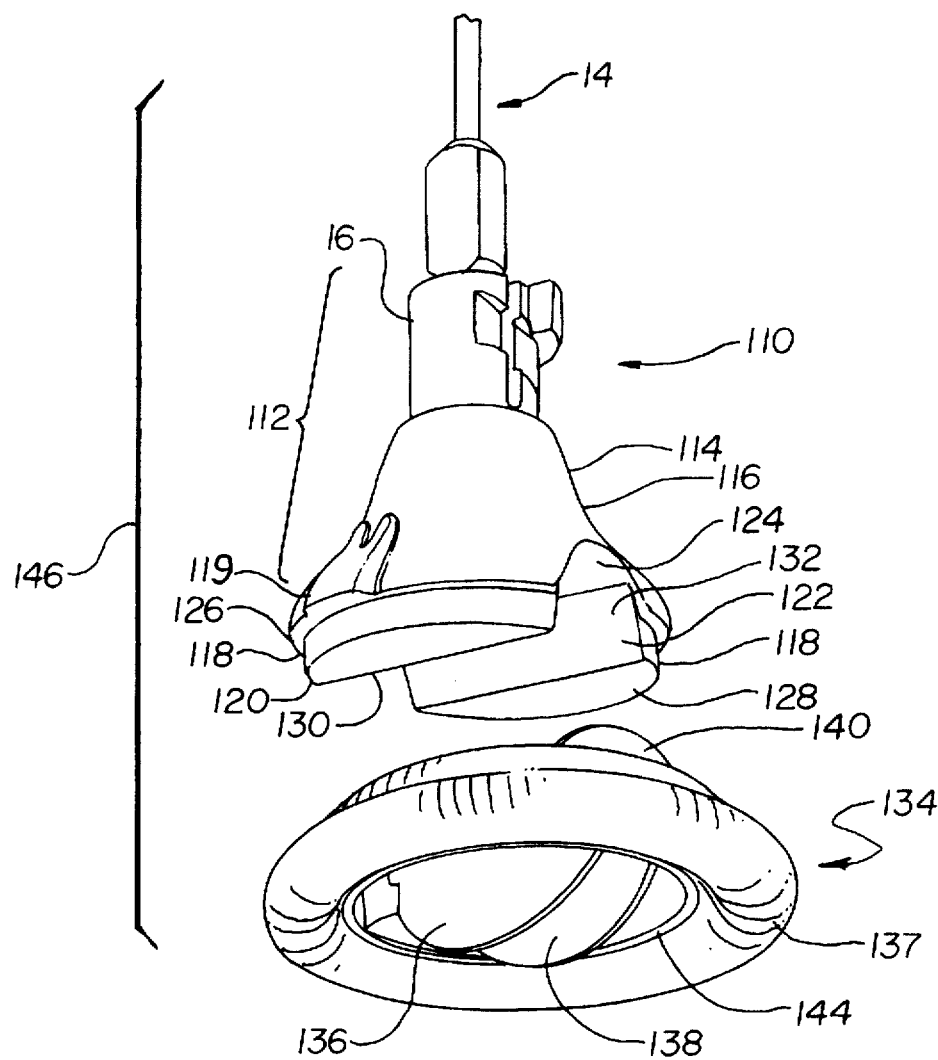
FIG. 8 is a perspective view of an alternative embodiment of the holder/rotator tool positioned above a mitral mechanical heart valve.
Figure 9:
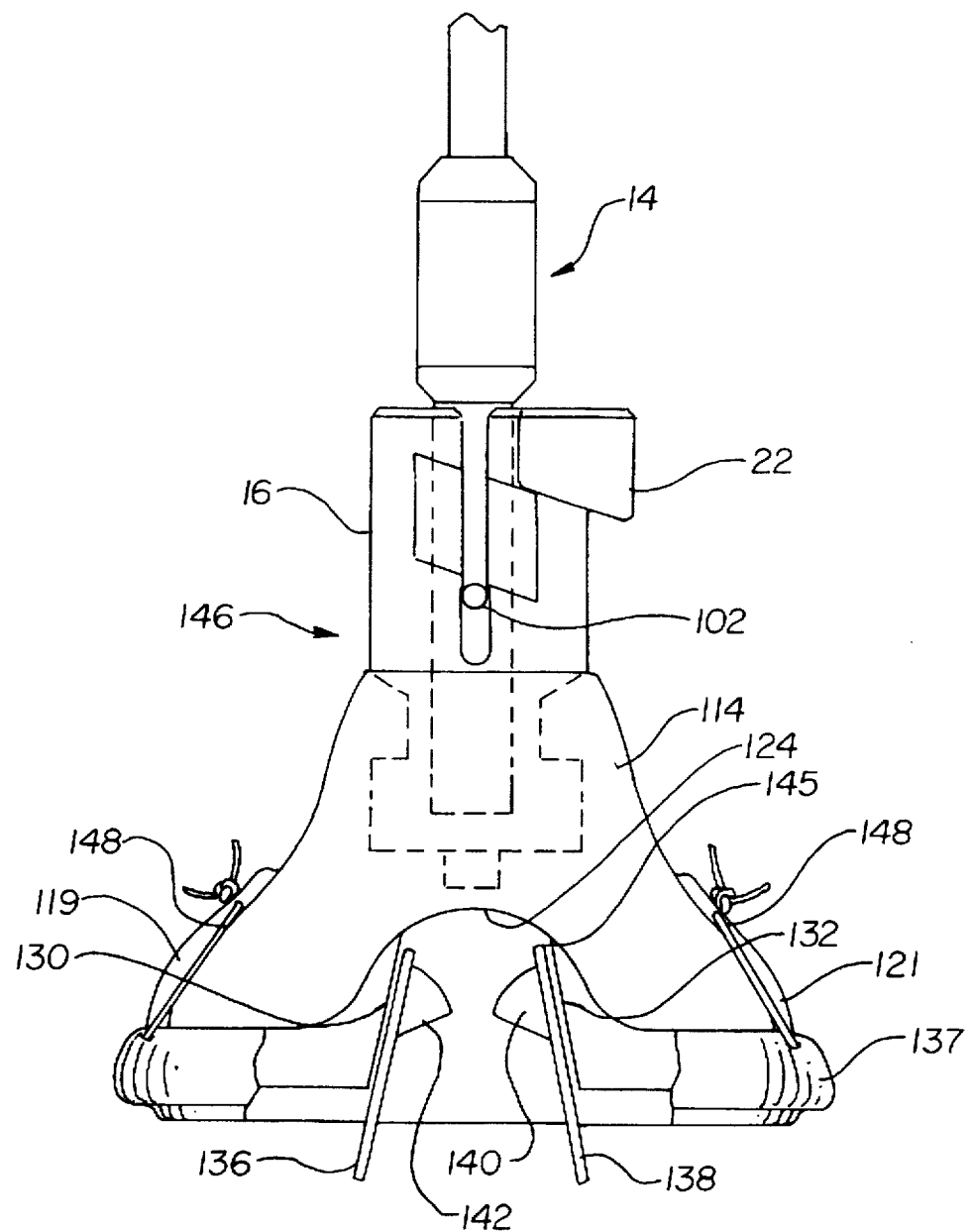
FIG. 9 is a side elevation view of the holder/rotator tool and mechanical heart valve assembly shown in FIG. 8 with sutures extending between the mechanical heart valve and the rotator head.

FIGS. 8 and 9 show an alternative embodiment of a rotator head for use with mitral mechanical heart valves. The holder/rotator tool assembly 110 comprises holder handle 14 and holder/rotator 112. The holder/rotator 112 comprises a rotator post 16 and a rotator head 114. It will be appreciated that the holder handle 14 shown and described above with regard to FIGS. 1–7 may likewise be utilized with the holder/rotator 112 shown in FIGS. 8 and 9. Moreover, the rotator post 16 described above with regard to FIGS. 1–7 may similarly be utilized as a part of the holder/rotator 112 shown in FIGS. 8 and 9.

As with the embodiment shown in FIGS. 1–7, the rotator head 114, which is likewise formed of a soft, conformable material, such as silicone, a soft plastic, or an elastomeric material, is molded about lower portion 38 of rotator post 16. While the upper portion 116 may comprise various configurations, it is preferably generally bell-shaped, and comprises suture shoulders 119, 121 similar to those provided in the first embodiment described herein. The sewing cuff 137 of the heart valve 134 is sutured to the suture shoulders 119, 121 on the rotator head 114 with sutures 148 to form an assembly 146, which is packaged as discussed above. Further, the mitral heart valve holder/rotator 112 shown in FIGS. 8 and 9 is used in substantially the same manner as the aortic heart valve holder/rotator 12 described with reference to FIGS. 1–7.

In this embodiment, however, in order to accommodate a mitral mechanical heart valve 134 as shown in FIG. 8, the lower portion 118 of the rotator head 114 has a gripping surface comprising two generally semi-circular protrusions 120, 122. The lower gripping surface 124 of upper portion 116 has an arched configuration, which cooperates with the semi-circular protrusions 120, 122. As best seen in FIG. 8, the protrusions 120, 122 have annular side walls 126, 128 and substantially vertical side walls 130, 132.

The mitral, rotatable mechanical heart valve 134 illustrated in FIGS. 8 and 9 has two leaflets 136, 138. When the valve 134 is assembled to the rotator head 114 to form the assembly 146 shown in the cut-away view in FIG. 9, the leaflets 136, 138 are disposed in an open position, and the arched lower surface 124 of rotator head 114 is adjacent pivot guards 140, 142 of heart valve 134. The protrusions 120, 122 are positioned on either side of the open leaflets 136, 138 such that the annular side walls 126, 128 are positioned against the inside orifice 144 of the heart valve 134. The protrusions 120, 122 do not extend through orifice 144.

As may be seen in FIG. 9, the vertical side walls 130, 132 of the protrusions 120, 122 are disposed substantially adjacent to, but not in contact with, the leaflets 136, 138. A gap 145 exists between the rotator head 114 and leaflets 136, 138 so that pressure is not applied directly to the leaflets 136, 138. In this way the holder/rotator 112 will not damage the valve leaflets 136, 138.

It is also within the contemplation of the invention that the holder/rotator tool comprise a limited slip mechanism which functions between the holder handle and the conformable rotator head to limit the amount of torque which can be applied to the valve. The limited slip mechanism acts as a safety mechanism to prevent the surgeon from over-torquing the valve and possibly damaging the surrounding heart tissue.

In accomplishing this aspect of the invention, the rotator head, which is formed from a relatively soft material, may be fabricated separately from the rotator post. The relatively rigid rotator post is then assembled into a cavity in the upper surface of the rotator head to couple the rotator post and rotator head together to form the holder/rotator. The limited slip mechanism is provided as a result of the interaction of these two components.

For example, the tip of the rotator post may be fabricated with splines disposed in a radial pattern. The rotator head may be separately molded with an internal cavity likewise having splines along its internal surface such that when the rotator post is inserted into the rotator head, the splines on the post mesh with the splines in the internal cavity of the rotator head. Thus, if high enough loads are applied, a ratcheting effect results as the rotator head is twisted on the stationary post. The relative size, number, geometry, and relationship of the splines on the post tip and in the internal cavity may be varied in order to provide the torque effect desired. For example, the internal cavity may be provided with twice as many splines as the post tip, such that the splines of the post tip are disposed within every other one of the splines of the internal cavity.

The holder/rotator tool assembly 10, 110 of the present invention has numerous advantages over the devices currently available. Hard plastic heads, such as those utilized in prior art structures, may slip against the heart valve surface, especially if there is blood on the surface, thereby potentially damaging the heart valve which is to be implanted. The use of silicone or an elastomeric material for rotator head 18, 114 allows rotator head 18, 114 to engage and grip the heart valve surface to facilitate the smooth rotation of the rotatable heart valve. This is true even if there is blood on the surfaces of the valve. In addition, the rotator head 18 may be provided with a stiffening core 20. The stiffening core 20 minimizes deformation of the rotator head 18 during rotation of the valve 82, while the outer silicone or elastomeric layer protects the valve 82 from scratches or other damage.

The rotator head 18, 114 may be configured in different shapes for use with aortic 82 and mitral valves 134. The cuff 86, 137 of a rotatable valve 82, 134 may be secured to the suture shoulders 62, 64 of the holder/rotator 12, 112 with sutures 108, 148. During implantation surgery, these sutures 108, 148 may be easily cut and removed with the holder/rotator tool assembly 10, 110. No manual manipulation is required to ensure proper engagement of the rotator head 18, and 114 and the heart valve 82, 134 to provide the transmission of torque. Moreover, while no additional parts or handles, are required, the holder handle 14 may be utilized.

Use of the rotator post 16 also contributes several advantages to the holder/rotator tool assembly 10, 110. The rotator post 16 provides a hard plastic interface between the soft rotator head 18, 114 and the holder handle 14. The interface between the rotator head 18, 114 and the rotator post 16 may be designed to provide a secure engagement, or a limited slip mechanism, if so desired.

The rotator post 16 also includes a flange 22 and grooves 32 to aid in the positioning and support of rotator head 18, 114 and the attached heart valve 82, 134 in a packaging container. The flange 22 on rotator post 16 defines the proper orientation of the rotator head 18, 114 and the rotator post 16 within the packaging container, limits movement of the heart valve in the packaging container, and provides an area for gripping if the surgeon prefers to rotate the valve with his or her fingers, rather than using the holder handle 14.

The cross pin passageways 26, 28 accept the cross pin 102 with a snap-fit engagement, ensuring the surgeon that the rotator post 16 and the holder handle 14 are securely coupled together. As a result, heart valve 82, 134 may be rotated in either direction. Also, the snap-fit engagement permits the reusable holder handle 14 to be disengaged from the holder/rotator 12, 112 with reasonable effort. The holder handle 14 may then be sterilized for reuse.

The holder handle 14 facilitates removal of both rotatable and non-rotatable heart valves from their packaging containers without touching the valves. Inasmuch as a single holder handle 14 may be used for either type of heart valve, its use eliminates the need for the surgeon to decide which holder handle to use, and reduces the number of tools and accessories required in the surgical suite.

The holder handle 14 additionally holds the heart valve and aids in its rotation upon implantation. The malleable section of holder handle 14 permits the surgeon or other medical personnel to bend or adjust the handle 14 to a desired orientation.

Figure 10A:
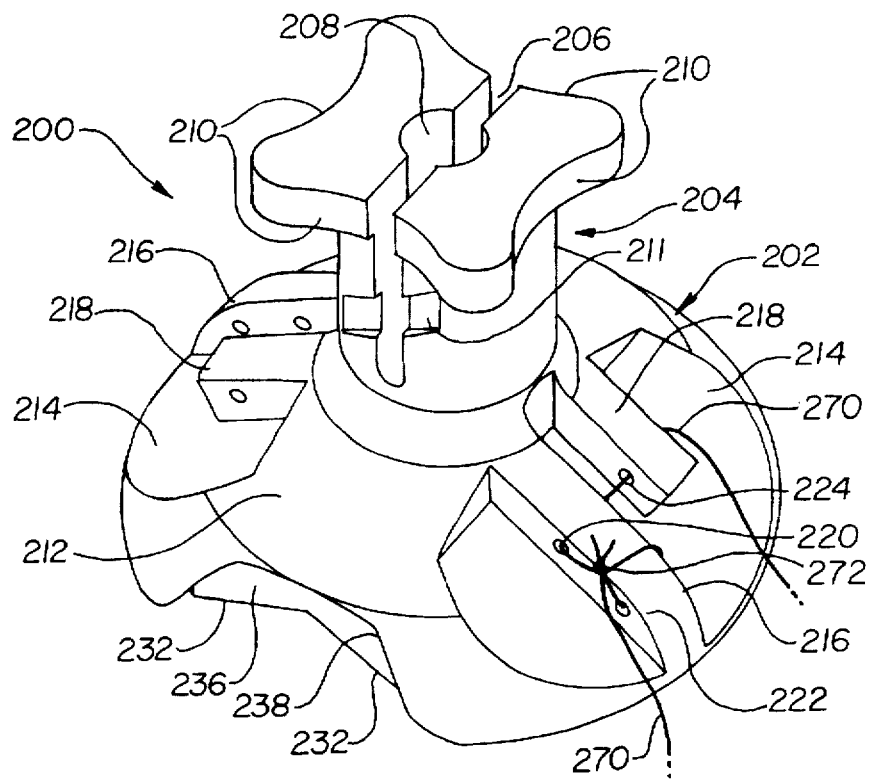
FIGS. 10A, 10B and 10C are top perspective, bottom perspective and side plan views, respectively of a mitral holder/rotator in accordance with another embodiment.
Figure 10B:
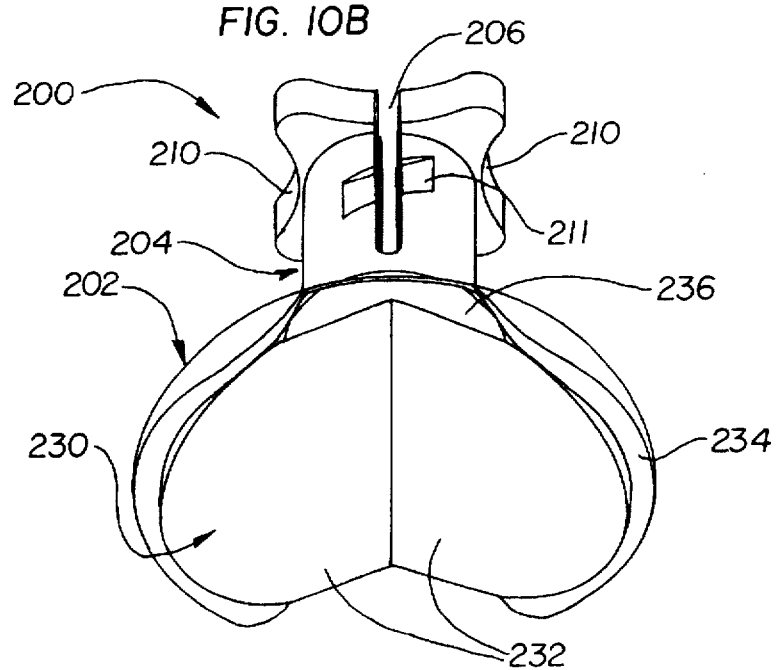
Figure 10C:
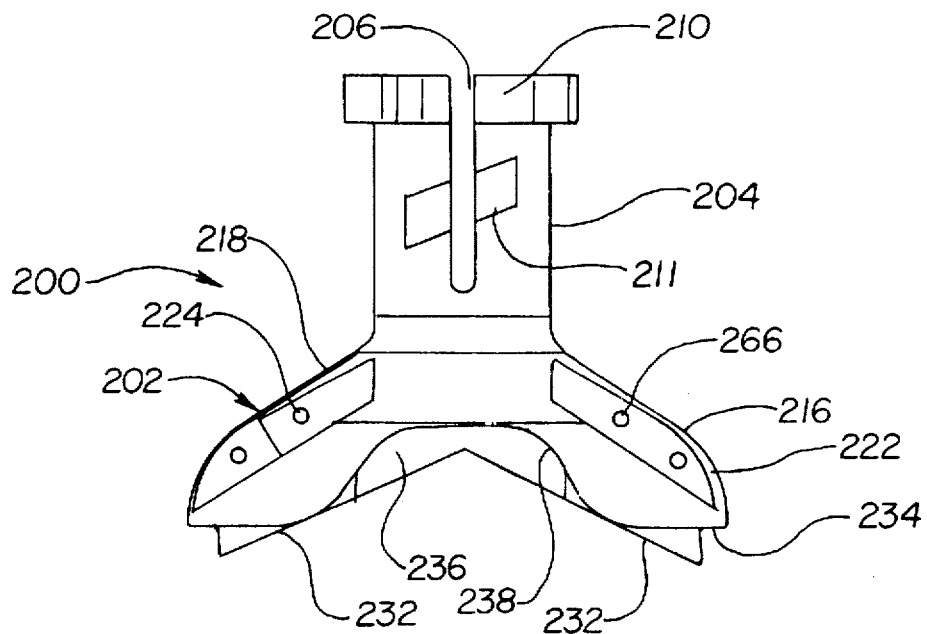

FIGS. 10A, 10B and 10C are top perspective, bottom perspective and side plan views, respectively, of holder/rotator 200 for a mitral heart valve prosthesis in accordance with another embodiment. It has been discovered that in some instances it is desirable to form a holder/rotator in accordance with the present invention from a rigid material, including a polyphenylsulfone, such as Radel®, polysulfone, such as Udel®, or any relatively hard plastic. Holder/rotator 200 includes head 202 formed, in one embodiment, integrally with post 204 extending axially from head 202. Post 204 includes a key way passageway 206 and bore 208 extending in an axial direction from the proximal end of post 204. The proximal end of post 204 includes finger grip surfaces 210 formed therein. Post 204 includes mounting groove 211 adapted for being received by a mounting arm of a packaging container (not shown) such that holder/rotator 200 may be suspended in the packaging container generally at post 204 at groove 211.

As shown in FIG. 10A, head 202 includes upper portion 212 having suture recesses 214 formed therein. Suture shoulders 216 and 218 extend in a generally outward direction radially from post 204 and are positioned in suture recess 214. In the embodiment shown, suture shoulder 218 is shorter than suture shoulder 216. Suture shoulder 216 includes suture holes 220 and 222 formed therein. A suture hole 224 is formed in shoulder 218 and is generally aligned with suture hole 220.

FIG. 10B shows lower portion 230 of head 202 which includes occluder conforming surfaces 232, circumferential lip 234, and pivot guard conforming surface 236. Occluder conforming surfaces 232 are shaped to conform to the surfaces of the occluder of the mitral heart valve prosthesis while maintaining the occluders in a substantially closed position. Lip 234 is of a size and shape to engage the annulus of the heart valve prosthesis. Similarly, pivot guard conforming surface 236 is of a size and shape to receive a pivot guard of the prosthesis. Pivot guard conforming surface 236 includes lip 238, shown in FIG. 10C, which substantially conforms to the pivot guard of the prosthesis (such as prothesis 82 shown in FIG. 1). Thus, when a torque is applied to holder/rotator 200, the torque is transferred to the prosthesis through the pivot guards by pivot guard conforming surface 236 and lip 238. This substantially reduces or eliminates the forces applied to the occluder leaflets.

Figure 11:
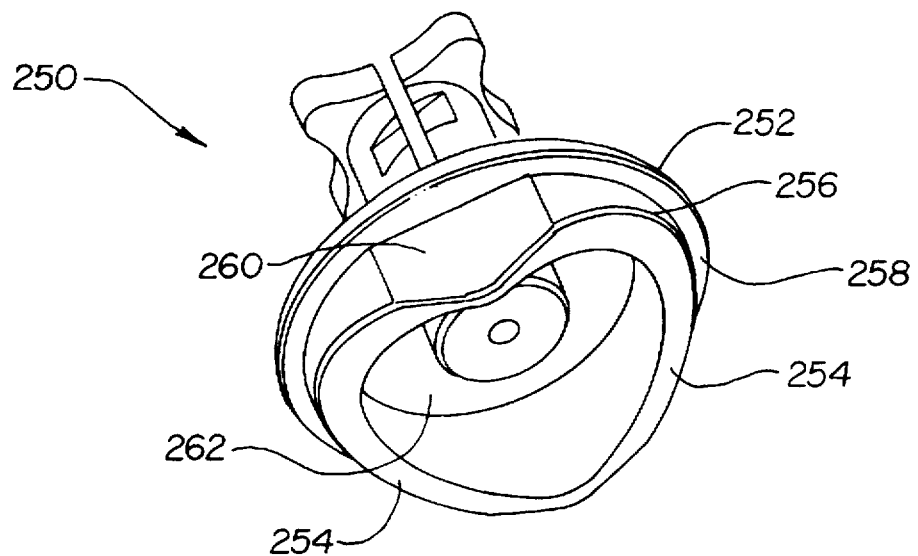
FIG. 11 is a bottom perspective view of an aortic holder/rotator.

FIG. 11 is a bottom perspective view of holder/rotator 250 for an aortic heart valve prosthesis in accordance with the invention. Aortic holder/rotator 250 is similar to mitral holder/rotator 200 shown in FIGS. 10A–10C and is formed of a rigid material. However, holder/rotator 250 includes head 252 having occluder conforming surfaces 254 adapted to maintain the occluders of an aortic prosthesis in a substantially closed position. Head 252 includes sidewall 256, lip 258 and pivot conforming surface 260. Pivot conforming surface 260 is adapted to fit proximate the pivots of the prosthesis and transmit a torque to the orifice body of the prosthesis. In the embodiment shown in FIG. 11, head 252 includes cavity 262 formed therein which reduces unnecessary mass and facilitates manufacturing using, for instance, injection molding techniques.

Referring back to FIG. 10A, a suture 270 is shown which extends through suture holes 220 and 224 and is used to couple the holder/rotator to the heart valve prosthesis, typically at the suture cuff of the prosthesis. Suture 270 extends through suture holes 220, 222, through the sewing cuff (not shown), and then through suture hole 224 and is knotted to suture shoulder 216 at knot 272. Holder/rotator 200 is removed from the prosthesis by cutting suture 270. Following the cutting of suture 270, suture 270 remains coupled to holder/rotator 200 by knot 272. The embodiment 250 in FIG. 11 may be similarly attached to the prosthesis.

Using a rigid material to form the holder/rotator of the present invention has been found to be particularly useful with aortic and/or relatively small prosthetic valves. However, the embodiment may be used with mitral prosthetic valves. In one preferred embodiment, the entire holder/rotator is formed as a unitary piece in a single injection molding step. The suture shoulders are recessed to reduce the likelihood that they will impinge on the native tissue.

Although the present invention has been described with reference to preferred embodiments, workers skilled in the art will recognize that changes may be made in form and detail without departing from the spirit and scope of the invention. For example, the keyed elements may be of any design and shape such as having a square cross section. Any type of attachment mechanism or suture shoulder may be used. In some embodiments, the handle may be fixedly attached to the holder/rotator. It will be understood that torque can be provided to the holder/rotator of the present invention with or without a handle. The holder/rotator set forth herein may be modified to function with any type of heart valve prosthesis. Further, any of the designs described herein may be manufactured with hard, soft or flexible material using any appropriate technique such as injection molding.

What is claimed is:

1. A device for engaging and gripping during implantation a heart valve prosthesis having two leaflets in an annulus with a substantially annular aperture therein, the prosthesis having a first perimeter and a second perimeter disposed on opposite sides of the annular aperture with the leaflets positioned therebetween, the device comprising:

an elongated handle having a proximal end and a keyed distal end;

an upstanding post extending in an axial direction having a proximal end and a distal end, the post comprising a substantially rigid material, the upstanding post having a keyed bore formed therein extending in the axial direction from the proximal end, the keyed bore adapted for receiving the elongated handle keyed distal end, the keyed bore shaped to substantially conform to the keyed distal end such that the keyed distal end of the elongated handle is moveable in the axial direction relative to the keyed bore and the keyed bore prevents rotation of the keyed distal end relative to the bore in a plane substantially perpendicular to the axial direction such that a torque applied to the handle is transferred to the post, and the handle is selectively removeable from the upstanding post; and a head integral with the distal end of the post, the head having a gripping surface configured to couple with the first perimeter and extend into the annulus a distance less than a distance to the second perimeter and generally conform to the leaflets, the gripping surface spaced apart from and not contacting the second perimeter, whereby the gripping surface of head may engage and grip the first perimeter of the heart valve prosthesis to facilitate rotation of the valve prosthesis relative to a sewing cuff during implantation.

2. The device of claim 1 wherein the leaflets meet at an angle along a diametral line of the annulus when in a closed position, and wherein the head has angled surfaces and substantially vertical sidewalls, the angled surfaces adapted for parallel relation with the leaflets of the heart valve prosthesis in the closed position.

3. The device of claim 2 adapted for use with a heart valve prosthesis having at least two pivot guards, the substantially vertical sidewalls adapted to be disposed substantially adjacent the pivot guards.

4. The device of claim 1 including at least one suture shoulder adapted for coupling the heart valve prosthesis to the device.

5. The device of claim 4 further comprising sutures for coupling the heart valve prosthesis to the suture shoulder.

6. The device of claim 5 adapted for use with a rotatable heart valve prosthesis having a sewing cuff rotatable relative to the annulus, wherein the sewing cuff may be coupled to the suture shoulder by the suture such that the suture may be cut to decouple the heart valve prosthesis from the suture shoulder and the device may be used to rotate the annulus relative to the sewing cuff during implantation.

7. The device of claim 1 wherein the keyed bore includes a key way passageway which extends substantially radially from an axis of the bore, and the keyed distal end of the handle includes a pin which extends substantially radially from an axis of the handle, the pin being engageable with the key way passageway.

8. The device of claim 1 wherein the post includes splines extending outward from the distal end of the post, the head being molded about the splines.

9. The device of claim 1 wherein the gripping surface comprises a soft elastomeric material.

10. The device of claim 9, wherein the head includes a stiffening core, the stiffening core comprising a rigid material covered by a soft elastomeric material.

11. The device of claim 10 wherein the distal end of the post comprises at least one axially extending stud, and the stiffening core comprises at least one bore, the at least one stud engaging the at least one bore to couple the stiffening core to the post.

12. The device of claim 1 wherein the gripping surface is formed of a rigid material.

13. A holder/rotator device for engaging and gripping during implantation of a heart valve prosthesis having two leaflets in an annulus with a substantially annular aperture therein, the prosthesis having a first perimeter and a second perimeter disposed on opposite sides of the annular aperture with the leaflets positioned therebetween, the device comprising:

an elongated handle having a proximal end and a keyed distal end;

an upstanding post extending in an axial direction to be substantially coaxial with an axis of the heart valve prosthesis, the upstanding post having a keyed bore formed therein extending in the axial direction from a proximal end, the bore adapted for receiving the elongated handle keyed distal end and shaped to substantially conform to the keyed distal end such that the keyed distal end of the elongated handle is moveable in the axial direction relative to the keyed bore and the keyed bore prevents rotation of the keyed distal end relative to the bore in a plane substantially perpendicular to the axial direction such that a torque applied to the handle is transferred to the post and the handle is selectively removeable from the upstanding post;

a head integral with a distal end of the post, the head having a gripping surface sized to couple with the first perimeter and extend into the annulus a distance less than a distance to the second perimeter, the gripping surface spaced apart from and not contacting the second perimeter, such that the head is configured to generally conform to the leaflets and couple to the first perimeter, the gripping surface adapted to engage and grip the first perimeter of the heart valve prosthesis to facilitate rotation of the valve prosthesis during implantation, such that a torque may be applied along the axis to the heart valve prosthesis to rotate the prosthesis in a sewing cuff relative to a natural tissue annulus of the heart following implantation;

a suture adapted to operably couple to the heart valve prosthesis; and a suture shoulder on the head for attaching the suture to the head and thereby adapted to attach the heart valve prosthesis to the head, whereby the head may be selectively withdrawn from the heart valve prosthesis by cutting the suture.

14. The device of claim 13 wherein the leaflets meet at an angle along a diametral line of the annulus when in a closed position, and wherein the head has angled surfaces and substantially vertical sidewalls, the angled surfaces adapted for parallel relation with the leaflets of the heart valve prosthesis in the closed position.

15. The device of claim 14 adapted for use with a heart valve prosthesis having at least two pivot guards, the substantially vertical sidewalls adapted to be disposed substantially adjacent the pivot guards.

16. The device of claim 13 wherein the head comprises a soft material.

17. The device of claim 16 wherein the head further comprises a stiffening core encompassed by the soft material, the stiffening core comprising a rigid material.

18. The device of claim 13 wherein the post further comprises a key way passageway which extends substantially radially from the keyed bore, and the handle comprises a pin which extends substantially radially from a rod, the pin being engageable with the key way passageway.

19. The device of claim 13 wherein the gripping surface is formed of a rigid material.

* * * * *